United States Patent [19]

Alstetter et al.

[11] Patent Number: 4,710,356

[45] Date of Patent: Dec. 1, 1987

[54] APPARATUS TO ACCELERATE THE TRANSFER OF MATERIAL BETWEEN TWO MEDIA REACTING IN A FLUIDIZED BED

[75] Inventors: Franz Alstetter, Karlsfeld; Guenther Hultsch, Oberschleissheim, both of Fed. Rep. of Germany

[73] Assignee: Krauss-Maffei A.G., Fed. Rep. of Germany

[21] Appl. No.: 685,233

[22] Filed: Dec. 21, 1984

[30] Foreign Application Priority Data

Dec. 23, 1983 [DE] Fed. Rep. of Germany ....... 3346861

[51] Int. Cl.$^4$ .................................................. B01J 8/18
[52] U.S. Cl. ...................................... 422/140; 422/145
[58] Field of Search ............... 422/140, 144, 145, 147; 431/7, 170; 432/15, 58; 34/57 A

[56] References Cited

U.S. PATENT DOCUMENTS

| | | | |
|---|---|---|---|
| 3,912,002 | 10/1975 | Elliott | 165/86 |
| 4,039,272 | 8/1977 | Elliott | 431/7 |
| 4,130,944 | 12/1978 | Hultsch et al. | 34/8 |
| 4,161,103 | 7/1979 | Horgan et al. | 437/7 |
| 4,282,009 | 8/1981 | Belke et al. | 422/145 |
| 4,343,624 | 8/1982 | Belke et al. | 422/142 |

FOREIGN PATENT DOCUMENTS

| | | | |
|---|---|---|---|
| 114474 | 9/1979 | Japan . | |
| 141379 | 11/1979 | Japan . | |
| 1581672 | 12/1980 | United Kingdom | 422/140 |

OTHER PUBLICATIONS

Lueger, "Lexicon der Verfahrenstechnik", (Enyclopedia of Process Technology) vol. 16, Fourth ed., p. 585.

Primary Examiner—Barry S. Richman
Assistant Examiner—William R. Johnson
Attorney, Agent, or Firm—Robert J. Koch

[57] ABSTRACT

A device for the acceleration of a reaction between media of solid and liquid phases comprising means for forming a fluidized bed, wherein the solid medium is held suspended in the liquid medium, and means for generating a centrifugal field for acting on the fluidized bed. The fluidized bed is defined between a rotating sieve drum and a first cylindrical sieve which is located within the sieve drum.

20 Claims, 4 Drawing Figures

APPARATUS TO ACCELERATE THE TRANSFER OF MATERIAL BETWEEN TWO MEDIA REACTING IN A FLUIDIZED BED

BACKGROUND OF THE INVENTION

The invention relates to an apparatus to accelerate the reaction between two media reacting in a fluidized bed.

It is known from the literature to increase the relative velocity between finely grained solid particles and a liquid carrier flow by means of a fluidized bed arrangement (see Lueger, "Lexicon der Verfahrenstechnik" ("Encyclopedia of Process Technology"), Vol. 16, Fourth Edition, page 585). However, particularly in the case of small particle sizes and small differences in density, the Archimedes numbers are so small that the transfer of material is only negligibly enhanced by a fluidized bed arrangement. In this case, the wetted solid particles remain surrounded by a boundary layer of the liquid and no relative velocity sufficient for a good transfer of material may be achieved within this boundary layer. The mechanism which then overwhelmingly determines the rate of the reaction is diffusion in the boundary layer.

SUMMARY OF THE INVENTION

It is therefore an object of the present invention to accelerate the chemical, biochemical, metallurgical or catalytic reaction between two media, the liquid and solid phases, by increasing the relative velocity at the boundary layers of the phases. Thus, the rates of material transfer particularly in the case of media with small particle size and/or small differences in density are also enhanced.

This object is attained by means of the apparatus according to the present invention. While an increase in the Archimedes number by only a factor of 5 may be obtained with conventional fluidized bed methods, the Archimedes numbers according to the invention may be increased in proportion to the centrifugal acceleration, i.e., a factor of at least 1000 for example. This leads to the advantage that good material exchange rates may be obtained in the field of biotechnology where, for example microbiological cultures grown on solid particles (bacteria, cells, enzymes, etc.) effect the transfer of material as in the treatment of waste waters by means of the so-called fermentation process.

In a preferred embodiment, a fluidized bed is formed subject to a centrifugal field by the cylindrical sieve of a rotatable sieve drum. The drum is provided with means for generating a pressure gradient. A first phase which maintains a second phase in suspension passes through the cylindrical sieve essentially in the radial direction and flows through the second, suspended phase. Uniform flow conditions over the entire surface of the fluidized bed are assured by means of the cylidnrical sieve surface and the flow pressure drop it produces. The arrangement of feed and discharge means thus presents no techical difficulties and a continuous operation of the fluidized bed arrangement according to the invention is possible.

In order to accelerate the reaction between two media—a flowing medium with a lower density and a suspended phase with a higher density—it is appropriate to design the sieve drum so that the pressure gradient necessary for the flow may be controlled in a simple manner. According to the invention, this is achieved by adjustment of a first skimming tube and/or filling an annular chamber to a greater height.

The reaction chamber according to the invention is preferrably bounded by a second, radially disposed inner cylindrical sieve. The fluidized bed flow in the reaction chamber may thus be kept free of the flow interferences caused by the first skimming tube. The radially disposed inner perforated cylinder according to the invention may be equipped with filter medium means, so that even the finest particles are retained in the reaction space.

According to another advantageous embodiment of the invention, an annular chamber and a feed line are designed as a closed system. This allows an admission pressure to be applied to the flowing medium in addition to the hydrostatic pressure of the radial liquid column. Similarly, a negative pressure may be applied for short periods of time for countercurrent rinsing of the filter medium.

It is possible, according to a further embodiment, to introduce a gaseous reaction medium, such as finely distributed oxygen for example for the execution and acceleration of aerobic processes, such as the biological decomposition of harmful substances in waste waters.

According to a further embodiment of the invention, it is possible to add other solid and/or liquid reaction media to the reaction space, continuously or periodically. Thus, additional reaction media may be fed into the reaction space directly through the internal space of the sieve drum or through the feed lines of the solid and/or liquid phases.

According to a particularly advantageous embodiment, all liquid and/or solid media may be processed independent of their densities with only one apparatus.

Preferably, the apparatus according to the invention is equipped with filter medium means to retain the fine particles entrained by the flowing phase.

Further objects, features and advantages of the present invention will become apparent from the detailed description of preferred embodiments which follows, when considered together with the attached figures of drawing.

BRIEF DESCRIPTION OF THE DRAWINGS

In the drawings:

According to FIGS. 1, 3 and 4, a sieve drum 2 is fastened to a rotatably supported shaft 1. The sieve drum comprises essentially a drum bottom 3, a drum wall 4 and an annular rim 5. A radially inner and radially outer perforated cylinder 6 and 7 are arranged within the sieve drum 2. The cylinders enclose a reaction space 8. A pressure chamber 9 is connected radially outside of the outer cylindrical sieve 7. The pressure chamber is connected with an annular chamber 11 axially following the drum bottom 3 by means of a circulation bore 10. An annular discharge chamber 12, axially outside an annular rim 5, communicates with the reaction chamber 8 by means of a radially outer discharge bore 13, according to the embodiment in FIG. 1. In the embodiment according to FIG. 3 the discharge chamber is connected with the reaction chamber by means of a radially inner discharge bore 14. The embodiment according to FIG. 4 has both radially inner and the radially outer discharge bores 13 and 14 in the annular rim 5. The discharge bores may be alternately closed by means of a stopper 15. In FIG. 4, the radially inner discharge bore 14 is closed, so that the sieve drum 2 functionally corresponds to the embodiment according to FIG. 1.

Figure 1:
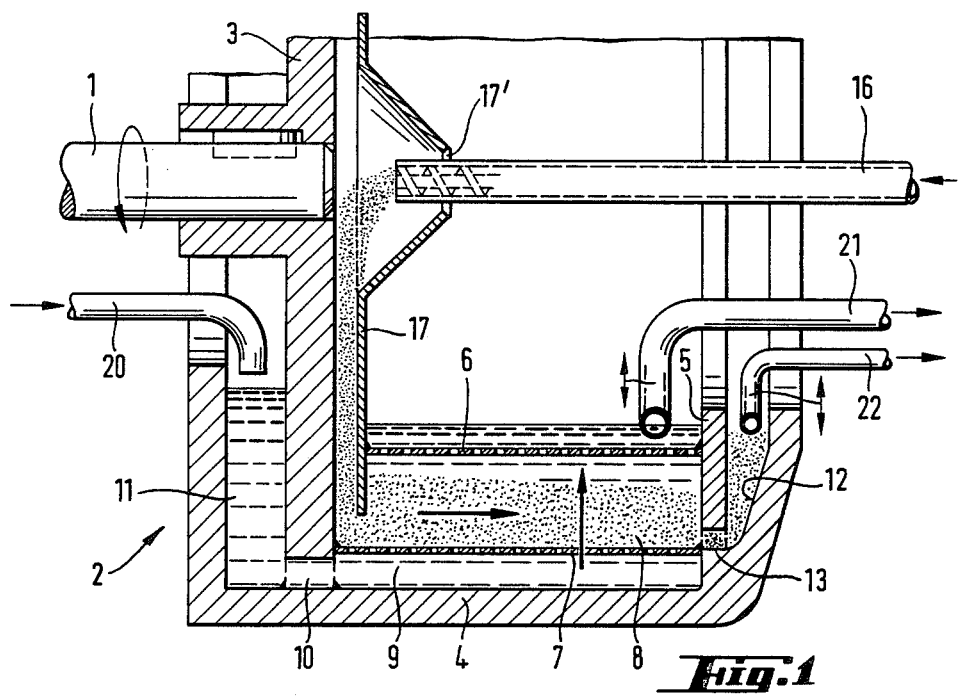
FIG. 1 shows a longitudinal section through a fluidized bed sieve drum.

According to FIGS. 1–4, a central filling pipe 16, secured against rotation, extends into the internal space of the sieve drum 2. The filling pipe opens into a central orifice 17' of a guide disk 17 mounted parallel to and spaced apart from the drum bottom 3. At its outer edge, the guide disk 17 forms an annular orifice with the drum bottom 3. The orifice leds into the reaction space 8. The central filling pipe 16 may be optionally equipped with a conveyor screw.

Figure 2:
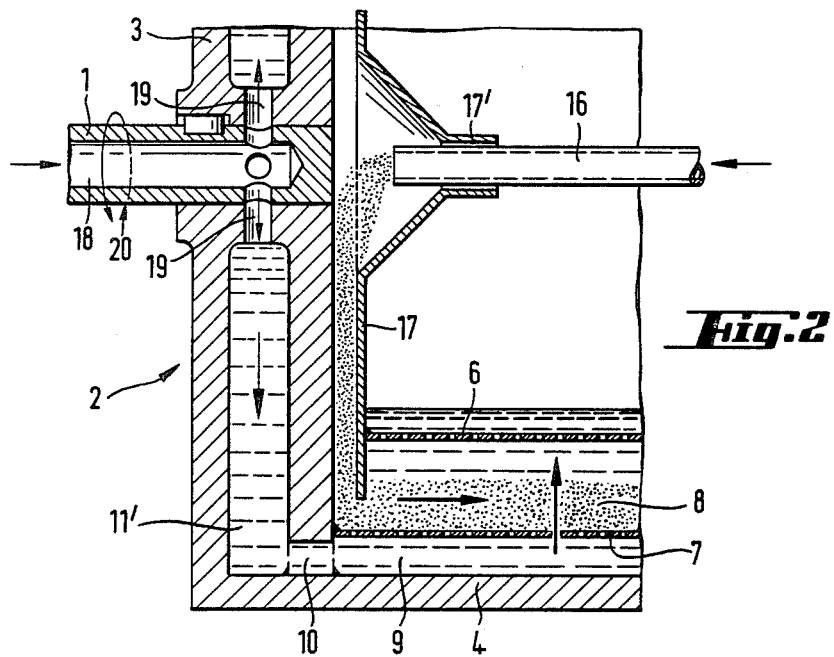
FIG. 2 shows a longitudinal section through a partial area of a fluidized bed sieve drum with an annular chamber according to another embodiment of the invention.

According to FIG. 2, the shaft 1 is provided with a bore 18, from which radially oriented channels 19 are provided which lead into a closed annular chamber 11'.

According to FIG. 1, a feed line 20 opens into the annular chamber 1. A first skimming tube 21 projects into the inner space of the sieve drum. The skimming orifice of the tube 21 may be adjusted in the radial direction, in steps if necessary. A second skimming tube 22 projects into the annular discharge chamber 12. The second tube can also be arranged in a radially adjustable manner.

The embodiments according to FIGS. 1 and 2 are suitable for accelerating a reaction between two media, in which a flow phase has a lesser density and a suspended phase, which is suspended in a centrifugal field in a fluid bed, has a greater density.

The fluid bed is formed in the embodiment according to FIG. 1 by passing the phase with the lower density through the line 20 and into the annular chamber 11. A liquid column of a given radial height is thus established in the chamber 11. The phase with the lower density flows through the circulating bore 10 and into the pressure chamber 9. From there, the phase with the lower density flows radially inward through the radially outer cylindrical sieve 7, so as to impact the phase with the higher density and maintain the latter in suspension. The higher density phase passes through the central filling pipe 16, through the intermediate space formed by the drum bottom 3 and the guide disk 17, into the reactor chamber, and is distributed in a suspended flow over the radially outer sieve surface 7. The lower density phase, which flows radially inward through the higher density phase, is removed following reaction in the reaction chamber 8 by the first skimming tube 21 at the radial height of the annular rim 5 and discharged to the outside. The higher density suspended phase travels in the axial direction to the radially outer discharge bore 13, and passes into the annular discharge chamber 12, from whence it is removed by the second skimming tube 22. In order to prevent interference with the fluid bed flow established in the reaction chamber 8 by the immersion of the first stripper tube 21, the radially inner cylindrical sieve 6 serves as a shielding device. A filter medium (not shown) may be arranged on the inner perforated cylinder in order to retain the fine particles entrained by the fluid bed flow.

The suspended state of the solid phase of higher density is obtained by a particular hydrostatic pressure gradient which is established between the annular chamber 11 and the reaction chamber 8. The pressure gradient is formed as a function of the density values of the two media and the rotating velocity of the sieve drum 2. This pressure gradient may be determined by the feed volume and by the radial height setting of the first skimming tube 21.

The pressure gradient creating the suspension may be obtained according to the embodiment of FIG. 2 by designing the annular chamber 11 as a closed system into which the phase of lower density may be introduced under pressure through a bore feed 18 and radially oriented channels 19. A higher hydrostatic pressure may be established in the annular chamber 11, which extends to the shaft 1, by means of a higher radial fluid column.

Figure 3:
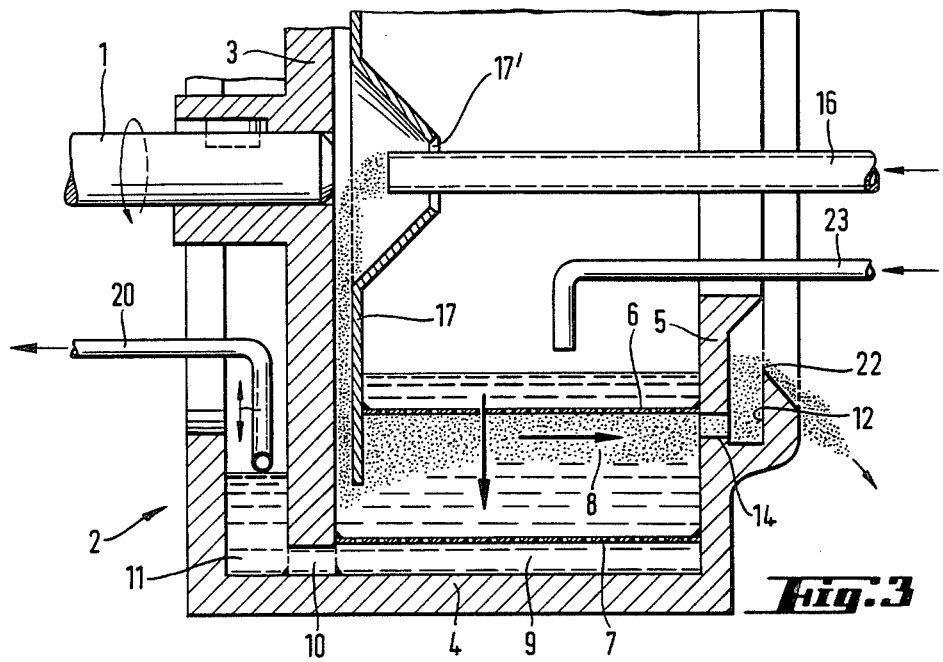
FIG. 3 shows a longitudinal section through a further embodiment of the fluidized bed sieve drum according to the invention.

The embodiment of the invention according to FIG. 3 is suitable for accelerating a reaction between two media, in which the flowing phase has a higher density and the phase suspended in a centrifugal field has a lower density.

The fluid bed is formed according to the embodiment of FIG. 3 as follows. The higher density phase is introduced into the inner space of the sieve drum 2 by means of a filling pipe 23. A radially outward directed flow enters through the radially inner cylindrical sieve 6 to impact the solid phase of lower density. The flow passes through the solid phase in a manner such that the latter is maintained in suspension over the radially inner cylindrical sieve 6. The lower density phase passes through the central filling pipe, through the space formed by the drum bottom 3 and the guide disk 17, and into the reaction chamber 8. From there lower density phase is distributed in a floating flow motion over the radially inner cylindrical sieve 6. The higher density phase, which flows through the lower density phase in the radially outward direction, reaches the pressure chamber defined by the drum wall 4, from whence it flows through the circulation bore 10 and into the annular chamber 11. The fill height in the annular chamber 11 is determined by the line 20, which acts as a skimming tube and removes the higher density phase at a particular radial height. A hydrostatic pressure gradient is thus established between the reaction chamber 8 and the annular chamber 11. The pressure gradient effects the outwardly directed flow of the higher density phase.

The discharge of the lower density phase, which is conveyed by the fluid bed through the radially inner discharge bore 14 into the annular discharge chamber 12, may be carried out by a radially and, if need be, intermittantly adjustable second skimming tube 22 (FIG. 1). As shown in FIG. 3, the lower density phase may also be discharged over a discharge edge 22'; as the lower density phase rises to the surface in the annular discharge chamber 12, it is automatically conveyed over the discharge edge.

The radially outward directed flow of the higher density phase may be achieved or promoted according to the embodiment of FIG. 2, in that the centrifuge space is designed as a closed system and exposed to an overpressure. The liquid phase is thereby conveyed into the space outside the centrifuge under normal pressure.

To retain the fine particles entrained by the fluid bed flow, a radially outer perforated cylinder 7 may be provided, which may optionally be covered by filter medium means.

Figure 4:
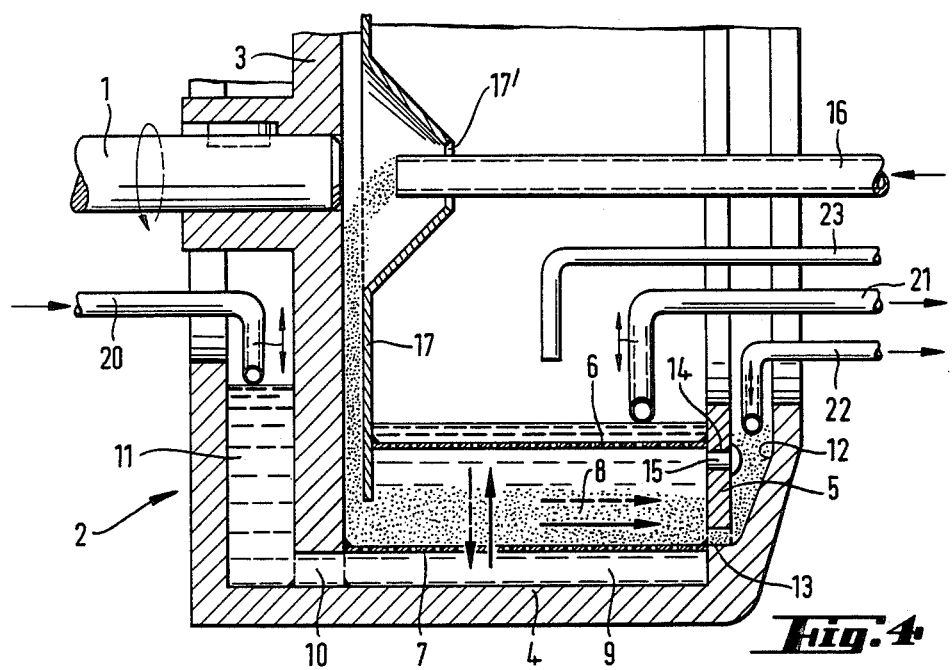
FIG. 4 shows a longitudinal section through a general embodiment of a fluidized bed sieve drum according to the invention.

The embodiment according to FIG. 4, represents a combination of the embodiments according to FIG. 1 and 3. In this embodiment, the feed line 20, which extends into the annular chamber 11, may also be used as a stripper tube with a radially adjustable skimming orifice. Both a filling pipe, corresponding to the embodiment of FIG. 3, and a first skimming tube 21, corresponding to the embodiment of FIG. 1, extend into the internal space of the sieve drum 2. When the radially outer discharge bore 13 is open, the fluid bed sieve drum is operable as in the embodiment of FIG. 1. The line 20 may serve as the feeder line for the lower density phase while the feeder pipe 23 remains idle. The first skimming tube 21 may serve as the outlet for the lower density phase after its flow through the reaction chamber 8. The flow direction of the two media of different density which flow through each other is indicated by the arrows with solid lines.

If the radially outer discharge bore 13 is closed instead of the radially inner discharge bore 14, the fluid bed sieve drum is operated as in the embodiment of FIG. 3. In this case, line 20 is used as a skimming tube and filter pipe 23 is employed in place of the first skimming tube 21. The flow direction of the two converging media of different densities is represented by arrows with broken lines.

As in the embodiment of FIGS. 1 and 3, the embodiment according to FIG. 4 may also be equipped with a closed annular chamber according to FIG. 2, into which the medium may be fed under pressure or from which it may be removed, through the bore 18 and the channels 19, by means of a reduced pressure.

Further reactants may be introduced into the reaction chamber in the gaseous, liquid or solid state through the feed lines of all of the embodiments—such as the central filling line 16, the bore 18 with the channels 19, the line 20 serving as the feeder line and the filler pipe 23. Thus, for example, for the execution and acceleration of aerobic processes, such as the biological decomposition of harmful substances in waste waters, finely distributed air may be introduced through the bore 18 and conveyed through the radially outer sieve surface 7 to the reaction chamber 8. Similarly, catalytically active solids may be introduced into the reaction chamber through the central filling pipe 16 and the guide disk 17. In principle, all types of additional reactants may be fed into the central inner space of the fluid bed sieve drum or the annular chamber 11 through separate lines.

As a rule, the suspended phase will consist of finely grained solid particles, kept in suspension by the flowing phase, the reaction liquid of the fluidized bed or vortex layer.

In principle, a medium which has a higher density than another medium may have a lower specific weight by virtue of gas formation or gas bonding allowing it to float. In this case, the embodiment of FIG. 3 is preferred, in which the phase tending to float is treated as a phase of lower density.

What is claimed is:

1. A device for the acceleration of a reaction between media of solid and liquid phase, comprising:
   means for forming a fluidized bed, wherein a solid medium is held suspended in a liquid medium, including
   a sieve drum,
   a first cylindrical sieve disposed within the sieve drum,
   means for controlling operational parameters for creating a pressure drop so that the liquid medium passes radially through said first cylindrical sieve and maintains the solid phase in suspension;
   means for generating a centrifugal field for acting on the fluidized bed including a shaft means for rotating said sieve drum and said first cylindrical sieve about a vertical axis of the sieve drum;
   means for introducing the liquid medium outside the first cylindrical sieve;
   means for defining a reaction chamber disposed radially inward of said first cylindrical sieve having a top and a bottom;
   a drum bottom of said sieve drum for bounding the bottom of the reaction chamber;
   an annular rim for bounding the top side of the reaction chamber;
   means for defining an annular discharge chamber above the top of the reaction chanber;
   means for defining a first discharge bore in said annular rim disposed at substantially the same radial height as the first cylindrical sieve, and for connecting the discharge chamber with the reaction chamber;
   means for defining a pressure chamber between said first cylindrical sieve and said sieve drum having a top bounded by said annular rim, and having a bottom bounded by the drum bottom;
   means for defining a second annular chamber disposed below the drum bottom; bottom;
   means for defining a circulation bore for connecting the second annular chamber with the pressure chamber;
   an inner second cylindrical sieve for defining a radially-inward side of said reaction chamber disposed radially inward of said discharge bore;
   wherein said means for introducing the liquid medium comprise a feed line for introducing the liquid medium into said second annular chamber, wherein the second annular chamber extends to a radial region near said shaft means, and wherein the feed line enters said chamber in the radial region near said shaft means; and
   means for introducing the solid medium into said reaction chamber comprising a central filling pipe.

2. A device according to claim 1, wherein said means for introducing the solid medium further comprises a conveyor screw disposed within said filling pipe.

3. A device according to claim 1, further comprising means for introducing an additional reaction medium enriched with a reactive gas into the sieve drum and radially within said inner cylindrical sieve.

4. A device according to claim 1, further comprising:
   means for defining an inner space radially inward of said inner second cylindrical sieve;
   a second filling pipe for introducing a second liquid medium denser than the solid medium into the inner space;
   means for closing said first radially adjustable skimming tube;
   means for defining a second discharge bore disposed substantially at the same radial height as said radially inner second cylindrical sieve for connecting said reaction chamber with said annular discharge chamber;

means for alternately closing said first and second discharge bores;

wherein said feed line may alternately function as a skimming tube for removing the second liquid medium from said second annular chamber when said first discharge bore is closed, said second discharge bore is open and the second filling pipe introduces the second liquid medium into the inner space, and wherein said first skimming tube is closed when said first discharge bore is closed, the second discharge bore open, and the second filling pipe introducing the second liquid medium into the inner space.

5. A device according to claim 1, further comprising a first radially-adjustable skimming tube for removing the liquid medium at a radial liquid level with respect to the axis of rotation less than a radial liquid level at which the liquid medium is introduced by said feed line; and a second radially-adjustable skimming tube for removing solid medium from said discharge chamber, wherein the solid medium flows from said reaction chamber to said discharge chamber through said discharge bore.

6. A device according to claim 5, wherein said radially-adjustable first and second skimming tubes are discontinuously adjustable.

7. A device according to claim 1, further comprising:
a guide disk facing said drum bottom, and means for defining a central orifice for holding said filling pipe; and
means for defining a space between the guide disk and said drum bottom for allowing the solid medium to pass from said central filling pipe to said reaction chamber.

8. A device according to claim 7, wherein said second annular chamber and said feed line comprise a closed system, and wherein the feed line further comprises:
a feed bore disposed within said shaft means;
a plurality of radial channels for connecting the feed bore with said second annular chambers;
a pressure means for providing a pressured source of liquid medium; and
a rotatable joint for connecting the feed bore with the pressure means.

9. A device according to claim 8, further comprising means for introducing a finely distributed gas phase reaction medium into said fluidized bed.

10. A device according to claim 9, wherein the gas phase reaction medium is introduced in said second annular chamber and is lead through said circulation bore and into said pressure chamber.

11. A device for the acceleration of a reaction betwen media of solid and liquid phase, comprising:
means for forming a fluidized bed, wherein a solid medium is held suspended in a liquid medium, including
a sieve drum,
a first cylindrical sieve disposed within the sieve drum,
means for controlling operational parameters for creating a pressure drop so that the liquid medium passes radially through said first cylindrical sieve and maintains the solid phase in suspension;
means for introducing the solid medium between said sieve drum and said first cylindrical sieve;
means for generating a centrifugal field for acting on the fluidized bed, including a shaft means for rotating said sieve drum and said first cylindrical sieve about a vertical axis of the sieve drum;

wherein the liquid phase has a greater density than the solid phase, and further comprising:
means for defining a reaction chamber having a top, a bottom and a radially-outward side bounded by said first cylindrical sieve;
a drum bottom of said sieve drum for defining the bottom of said reaction chamber;
an annular rim for defining the top of said reaction chamber;
means for defining an annular discharge chamber disposed above said annular rim;
means for defining a radially inward discharge bore within said annular rim and disposed at substantially the same radial height as said first cylindrical sieve for connecting the reaction chamber with the annular discharge chamber;
means for defining a pressure chamber disposed radially outward of said reaction chamber having a top bounded by the annular rim, a bottom bounded by the drum bottom, and a radially-outward side defined by the sieve drum;
means for defining a second annular chamber below the drum bottom;
means for defining a circulation bore for connecting the second annular chamber with the pressure chamber;
means for defining an inner space radially inward of said first cylindrical sieve;
a first filling pipe for introducing the denser liquid phase into the inner space;
a central second filling pipe for introducing the solid medium of lesser density;
a guide disk facing said drum bottom and having a central orifice for holding said central second filling pipe;
means for defining an annular outlet orifice between the guide disk and the drum bottom for connecting the bottom space with the reaction chamber;
means for defining a bottom space between the guide disk and said drum bottom for allowing the solid medium to pass from said central second filling pipe to said reaction chamber; and
an overflow edge for discharging the solid medium of lower density from the annular discharge chamber.

12. A device according to claim 11, further comprising an outer second cylindrical sieve disposed radially inward of said circulation bore for separating said reaction chamber from said pressure chamber.

13. A device according to claim 11, further comprising a radially adjustable skimming tube for removing the denser liquid medium from said annular chamber and thereby creating a pressure drop from said inner space to said pressure chamber.

14. A device according to claim 11, further comprising a filter means for preventing fine suspended particles from being discharged with said liquid medium in a discharge path of said liquid medium.

15. A device according to claim 11, wherein second annular chamber is a closed system, and further comprising:
a discharge bore disposed witnn said shaft;
a plurality of radial channels for connecting said annular chamber with the discharge bore;
wherein the remainder of the device also comprise a closed system capable of being pressurized.

16. A device according to claim 15, further comprising means for connecting said discharge bore with a pressure source in order that the device may be rinsed with a counter flow.

17. A device according to claim 16, wherein said means for connecting comprises a rotating joint.

18. A device according to claim 17, further comprising means for introducing a fine distribution of a gas phase reaction medium into both the liquid and solid reaction media.

19. A device according to claim 18, wherein said means for introducing comprises introducing the gas phase reaction medium into said first filling pipe.

20. A device according to claim 18, wherein said means for introducing comprises a plurality of gas injection nozzles distributed about the circumference of the sieve drum for injecting gas against the flow of the denser liquid medium.

* * * * *